(12) United States Patent
Lee et al.

(10) Patent No.: US 12,704,476 B2
(45) Date of Patent: Aug. 11, 2026

(54) SEMICONDUCTOR STRUCTURE, INTEGRATED CIRCUIT AND MANUFACTURING METHOD THEREOF

(71) Applicant: Taiwan Semiconductor Manufacturing Company, Ltd., Hsinchu (TW)

(72) Inventors: I-Che Lee, Hsinchu (TW); Huai-Ying Huang, New Taipei City (TW); Yen-Chieh Huang, Hsinchu (TW); Kai-Wen Cheng, Taichung City (TW); Yu-Ming Lin, Hsinchu City (TW); Chung-Te Lin, Tainan City (TW)

(73) Assignee: Taiwan Semiconductor Manufacturing Company, Ltd., Hsinchu (TW)

( * ) Notice: Subject to any disclaimer, the term of this patent is extended or adjusted under 35 U.S.C. 154(b) by 488 days.

(21) Appl. No.: 18/333,485

(22) Filed: Jun. 12, 2023

(65) Prior Publication Data

US 2024/0410854 A1 Dec. 12, 2024

(51) Int. Cl.
*G01N 27/414* (2006.01)
*G01N 33/00* (2006.01)
*H10W 20/41* (2026.01)

(52) U.S. Cl.
CPC ..... *G01N 27/4141* (2013.01); *G01N 27/4148* (2013.01); *G01N 33/005* (2013.01); *H10W 20/435* (2026.01)

(58) Field of Classification Search
CPC ........... G01N 27/4141; G01N 27/4148; G01N 33/005; H01L 23/5283
USPC ........................................................ 73/31.06
See application file for complete search history.

(56) References Cited

U.S. PATENT DOCUMENTS 4,608,549 A * 8/1986 Fukui ..................... G01N 27/12 438/794
6,111,280 A * 8/2000 Gardner ............... G01N 27/128 257/253

* cited by examiner

*Primary Examiner* — Nathaniel T Woodward
(74) *Attorney, Agent, or Firm* — JCIPRNET

(57) ABSTRACT

A semiconductor structure is disclosed. The semiconductor structure includes a semiconductor substrate, a hydrogen sensing stacked layer disposed over the semiconductor substrate, and a protection layer disposed on the hydrogen sensing stacked layer. The hydrogen sensing stacked layer comprises a hydrogen-free oxide layer and a metal oxide layer disposed on the hydrogen-free oxide layer.

20 Claims, 14 Drawing Sheets

520
510
513
532
531
530
521
512
511

520
550
552
551
542
541
532
531
530

SEMICONDUCTOR STRUCTURE, INTEGRATED CIRCUIT AND MANUFACTURING METHOD THEREOF

BACKGROUND

Gas sensor in semiconductors have received more attention due to their high sensitivity to gas. Specifically, when a gas sensor in semiconductors is exposed to a specific gas, its electrical characteristics will change accordingly. Therefore, by detecting the electrical characteristics of the semiconductor, the user can observe the environment in which the semiconductor is located.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DESCRIPTION OF THE EMBODIMENTS

Figures 1A, 1B, 1C:
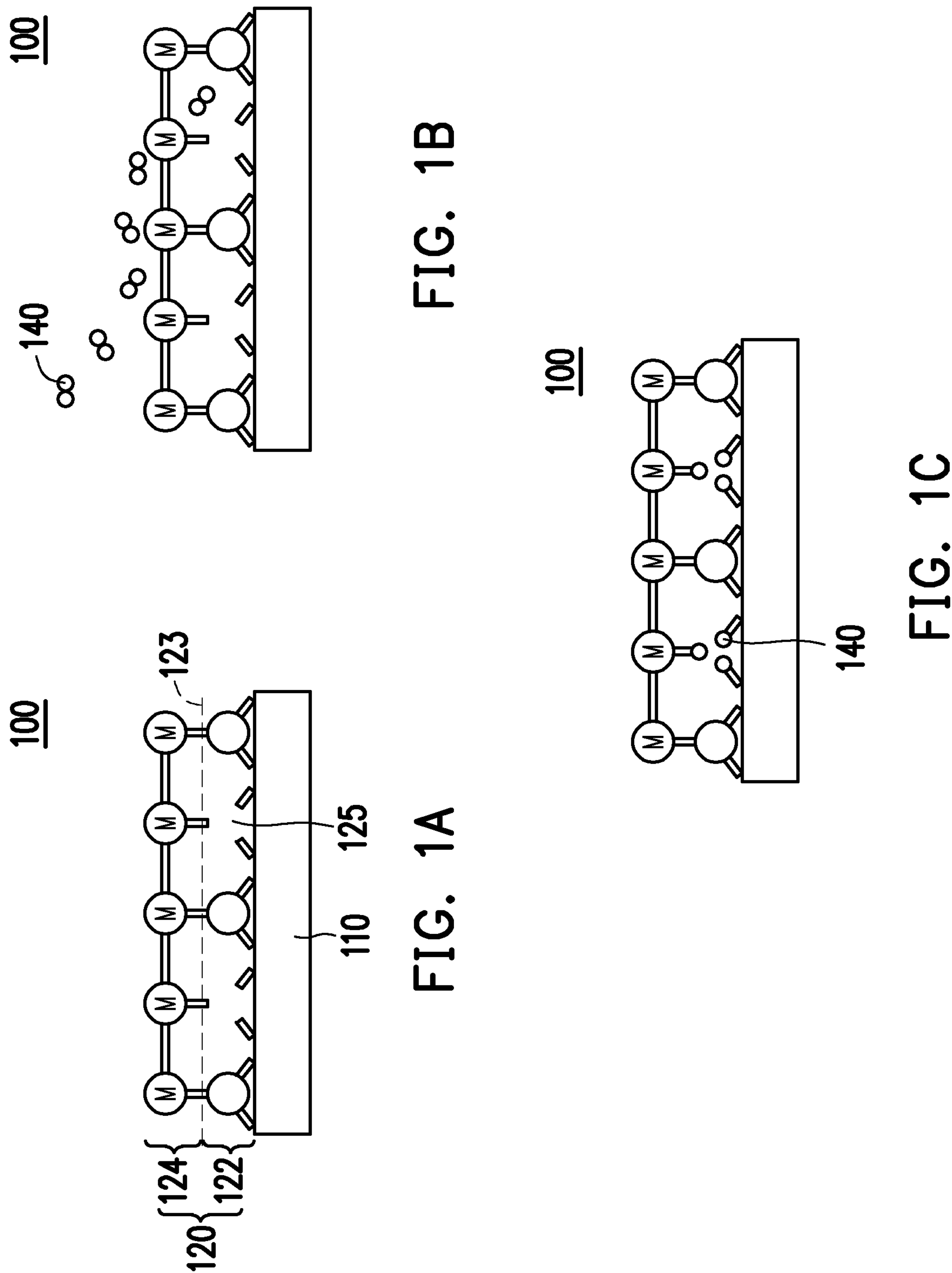
FIGS. 1A-1C illustrate schematic cross-sectional views of a hydrogen sensing mechanic of the hydrogen sensor according to some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Spatially relative terms, such as “beneath,” “below,” “lower,” “above,” “upper” and/or the like, may be used herein for ease of description to describe one element or feature’s relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The present disclosure is generally related to semiconductor structure, integrated circuits, and fabrication methods, and more particularly to fabricating the semiconductor structure or the integrated circuit for sensing hydrogen. Hydrogen gas is a flammable gas without color, odor, and taste, and thus cannot be sensed by the human senses in the atmosphere. Therefore, in order to safely use hydrogen, a hydrogen sensor is essential. Various types of hydrogen sensors have been reported. However, the hydrogen sensors among them are difficult to embed in conventional integrated circuits (ICs) due to their large size. In the present disclosure, a novel technology to form hydrogen sensors that can provide a smaller size structure and a more process friendly structures is provided.

FIGS. 1A-1C illustrate schematic cross-sectional views of a hydrogen sensing mechanic of a hydrogen sensor according to some embodiments of the present disclosure.

Referring to FIG. 1A, a hydrogen sensor 100 includes a carrier substrate 110 and a hydrogen sensing stacked layer 120. The hydrogen sensing stacked layer 120 is disposed on the carrier substrate 110. The hydrogen sensing stacked layer 120 includes a hydrogen-free oxide layer 122 and a metal oxide layer 124, and there is a hydrogen sensing interface 123 between the hydrogen-free oxide layer 122 and a metal oxide layer 124. The hydrogen-free oxide layer 122 is disposed between the carrier substrate 110 and the metal oxide layer 124.

The carrier substrate 110 may be a metal substrate, a semiconductor substrate, a dielectric substrate, or the like. For example, the material of the carrier substrate 110 includes a conductive material (e.g., copper, aluminum, metal alloys, etc.), a semiconductor material (e.g., silicon, germanium; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP; or combinations thereof), a dielectric material (e.g., glass, PTFE, sapphire, etc.), and/or the like.

The hydrogen-free oxide layer 122 is formed by performing an in-situ steam generation (ISSG) process in an ambient environment of oxide, $H_2O$, NO, combinations thereof, or the like. Thereby, the hydrogen-free oxide layer 122 does not comprise hydrogen atom.

The metal oxide layer 124 is formed by any suitable deposition process, such as, atomic layer deposition (ALD), chemical vapor deposition (CVD), high density plasma CVD (HDP-CVD), physical vapor deposition (PVD), and/or the like.

Since the hydrogen-free oxide layer 122 does not comprise hydrogen atom, weak bonding is formed at the hydrogen sensing interface 123 between the hydrogen-free oxide layer 122 and the metal oxide layer 124, and dangling bonds 125 are generated at the hydrogen sensing interface 123 accordingly, as shown in FIG. 1A.

Referring to FIG. 1B, the hydrogen sensor 100 is placed in the atmosphere containing a certain concentration of hydrogen 140. When the hydrogen sensor 100 is placed in the atmosphere of containing hydrogen 140, hydrogen 140 is caught by the hydrogen sensor 100. In this case, the hydrogen sensor 100 includes hydrogen 140 that has diffused or otherwise migrated from the metal oxide layer 124 to the dangling bonds 125 at the hydrogen sensing interface 123.

Then, referring to FIG. 1C, hydrogen 140 would be caught by the hydrogen sensor 100 at the hydrogen sensing interface 123 between the hydrogen-free oxide layer 122 and the metal oxide layer 124.

Figure 2B:
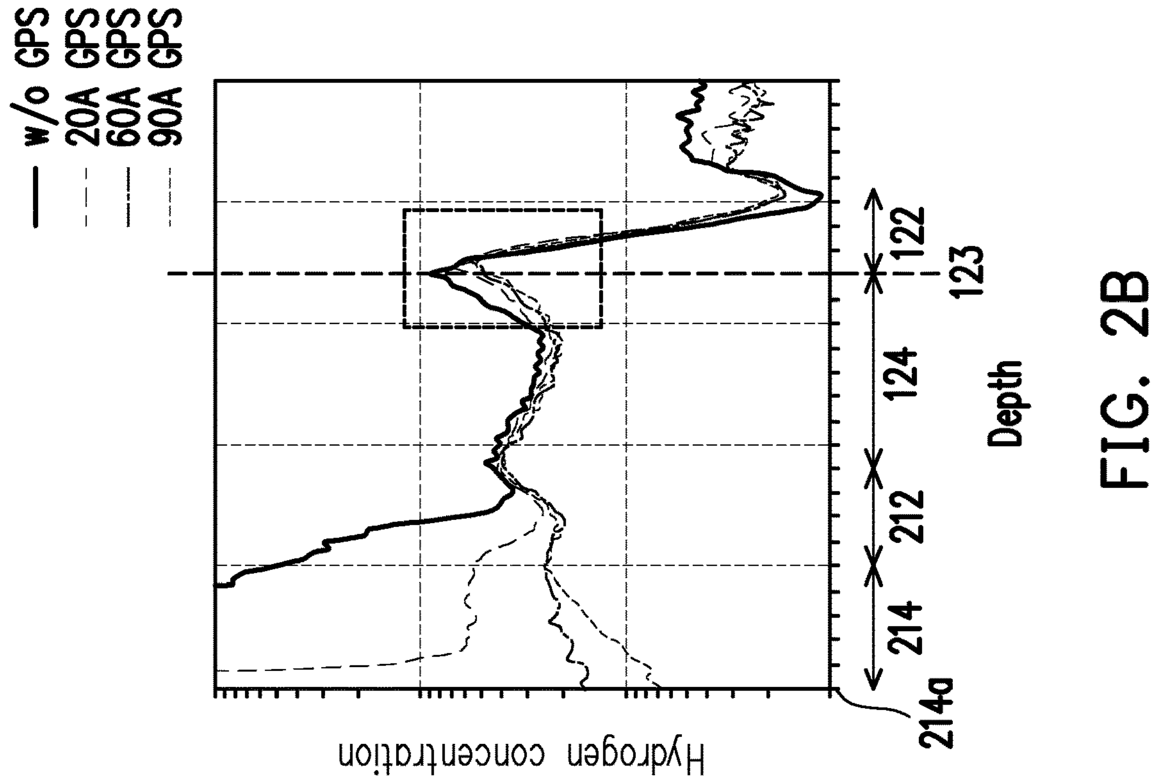
FIG. 2A illustrate schematic cross-sectional views of a semiconductor structure, and FIG. 2B illustrate a view showing a relationship between hydrogen concentration and a depth of a semiconductor structure according to some embodiments of the present disclosure.
Figure 2A:
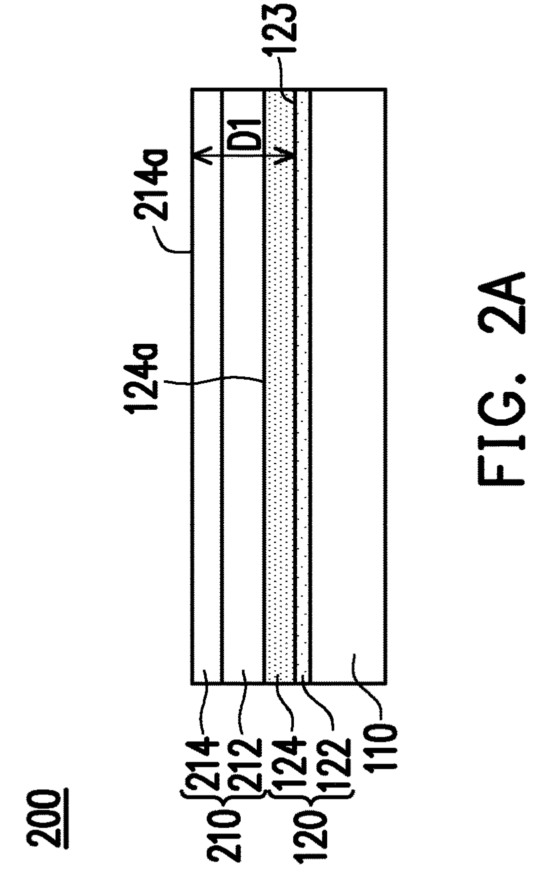

FIG. 2A illustrate schematic cross-sectional views of a semiconductor structure, and FIG. 2B illustrate a view showing a relationship between hydrogen concentration and a depth of a semiconductor structure according to some embodiments of the present disclosure.

Referring to FIG. 2A, a semiconductor structure 200 for sensing hydrogen is provided. The semiconductor structure 200 comprises a semiconductor substrate 110, a hydrogen sensing stacked layer 120, and a protection layer 210. The hydrogen sensing stacked layer 120 is disposed over the semiconductor substrate 110, and the protection layer 210 is disposed over the hydrogen sensing stacked layer 120. In other words, the hydrogen sensing stacked layer 120 is disposed between the semiconductor substrate 110 and the protection layer 210.

The semiconductor substrate 110 may be a semiconductor wafer or a semiconductor-on-insulator (SOI) wafer. In some embodiment, the semiconductor substrate 110 may be formed in a front-end-of-line (FEOL) process. In some embodiment, the semiconductor substrate 110 may be a silicon substrate including FEOL devices, such as active components (e.g., transistors or the like) and passive components (e.g., resistors, capacitors, inductors, or the like), formed therein.

The hydrogen sensing stacked layer 120 comprises a hydrogen-free oxide layer 122 and a metal oxide layer 124. The metal oxide layer 124 is disposed on the hydrogen-free oxide layer 122, and is between the protection layer 210 and the hydrogen-free oxide layer 122. There is a hydrogen sensing interface 123 located between the hydrogen-free oxide layer 122 and the metal oxide layer 124.

In some embodiment, the hydrogen-free oxide layer 122 may include silicon nitride, $Al_2O_3$, HfO, ZrO, or TiO, and may be formed by in-situ steam generation (ISSG) process. In some embodiment, the metal oxide layer 124 may include InGaZnO, InO, GaO, ZnO, AlO, SnO, or CuO, and may be formed by any suitable deposition process, such as, atomic layer deposition (ALD), chemical vapor deposition (CVD), high density plasma CVD (HDP-CVD), physical vapor deposition (PVD), and/or the like.

The protection layer 210 is disposed on the hydrogen sensing stacked layer 120. The protection layer 210 includes a stacked layer, and the stacked layer comprises a silicon oxide layer 212 and an aluminum oxide ($AlO_x$) layer 214. The silicon oxide layer 212 is disposed on a surface 124*a* of the metal oxide layer 124, and the aluminum oxide ($AlO_x$) layer 214 is disposed on the silicon oxide layer 212. In some embodiment, the protection layer 210 functions as a barrier layer or an etch stop layer that effectively blocks water or moisture from penetrating into the elements underlying thereto or damages from the subsequent manufacturing process(es) such as an etching process. In an alternative embodiment, the protection layer 210 may be optionally omitted; in other words, the hydrogen sensing stacked layer 120 is exposed in the atmosphere, and the disclosure is not limited thereto. In some embodiment, the material of the hydrogen-free oxide layer 122 is different from the material of the aluminum oxide ($AlO_x$) layer 214, and the material of the metal oxide layer 124 is different from the material of the aluminum oxide ($AlO_x$) layer 214.

A hydrogen sensing interface 123 is located between the hydrogen-free oxide layer 122 and the metal oxide layer 124. A distance D1 between the hydrogen sensing interface 123 and a surface 214*a* of the aluminum oxide ($AlO_x$) layer 214 may range from about 200 Å to about 2 μm. Within this range, hydrogen could diffuse through the silicon oxide layer 212 and the aluminum oxide ($AlO_x$) layer 214, to the hydrogen sensing interface 123 between the hydrogen-free oxide layer 122 and the metal oxide layer 124.

Next, as shown in FIG. 2B, a relationship between hydrogen concentration and a depth of a semiconductor structure is shown. The concentration of hydrogen in the semiconductor structure 200 may be analyzed by secondary ion mass spectrometry (SIMS) technology. It could be seen from FIG. 2B, hydrogen could diffuse through the aluminum oxide ($AlO_x$) layer 214 and the silicon oxide layer 212, and accumulate at the hydrogen sensing interface 123 between the hydrogen-free oxide layer 122 and the metal oxide layer 124.

Figure 3B:
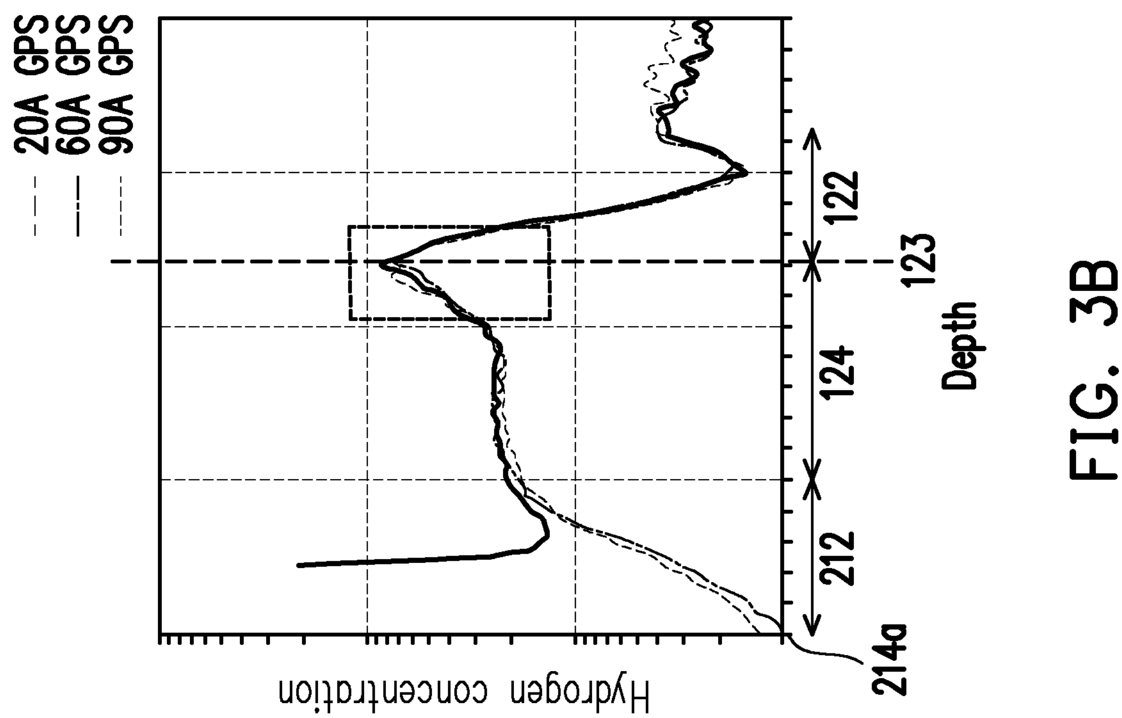
FIG. 3A illustrate schematic cross-sectional views of a semiconductor structure, and FIG. 3B illustrate a view showing a relationship between hydrogen concentration and a depth of a semiconductor structure according to some embodiments of the present disclosure.
Figure 3A:
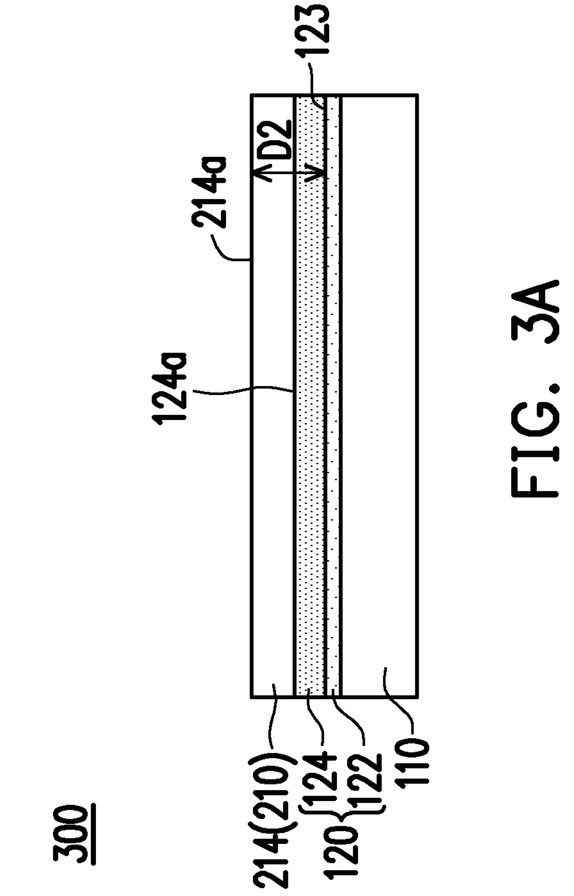

FIG. 3A illustrate schematic cross-sectional views of a semiconductor structure, and FIG. 3B illustrate a view showing a relationship between hydrogen concentration and a depth of a semiconductor structure according to some embodiments of the present disclosure.

Referring to FIG. 3A, a semiconductor structure 300 for sensing hydrogen is provided. The semiconductor structure 300 comprises a semiconductor substrate 110, a hydrogen sensing stacked layer 120, and a protection layer 210. The hydrogen sensing stacked layer 120 is disposed over the semiconductor substrate 110, and the protection layer 210 is disposed over the hydrogen sensing stacked layer 120. In other words, the hydrogen sensing stacked layer 120 is disposed between the semiconductor substrate 110 and the protection layer 210.

The semiconductor substrate 110 may be a semiconductor wafer or a semiconductor-on-insulator (SOI) wafer. In some embodiment, the semiconductor substrate 110 may be formed in a front-end-of-line (FEOL) process. In some embodiment, the semiconductor substrate 110 may be a silicon substrate including FEOL devices, such as active components (e.g., transistors or the like) and passive components (e.g., resistors, capacitors, inductors, or the like), formed therein.

The hydrogen sensing stacked layer 120 comprises a hydrogen-free oxide layer 122 and a metal oxide layer 124. The metal oxide layer 124 is disposed on the hydrogen-free oxide layer 122, and is between the protection layer 210 and the hydrogen-free oxide layer 122. There is a hydrogen sensing interface 123 located between the hydrogen-free oxide layer 122 and the metal oxide layer 124.

In some embodiment, the hydrogen-free oxide layer 122 may include silicon nitride, $Al_2O_3$, HfO, ZrO, or TiO, and may be formed by in-situ steam generation (ISSG) process. In some embodiment, the metal oxide layer 124 may include InGaZnO, InO, GaO, ZnO, AlO, SnO, or CuO, and may be formed by any suitable deposition process, such as, atomic layer deposition (ALD), chemical vapor deposition (CVD), high density plasma CVD (HDP-CVD), physical vapor deposition (PVD), and/or the like.

The protection layer 210 is disposed on the hydrogen sensing stacked layer 120. The protection layer 210 includes a single layer, and the single layer may comprise an aluminum oxide ($AlO_x$) layer 214. The aluminum oxide ($AlO_x$) layer 214 is disposed on a surface 124*a* of the metal oxide layer 124. In some embodiment, the protection layer 210 functions as a protect layer or an etch stop layer that effectively blocks water or moisture from penetrating into the elements underlying thereto or damages from the subsequent manufacturing process(es) such as an etching process. In an alternative embodiment, the protection layer 210 may be optionally omitted; in other words, the hydrogen sensing stacked layer 120 is exposed in the atmosphere, the disclosure is not limited thereto.

A hydrogen sensing interface 123 is located between the hydrogen-free oxide layer 122 and the metal oxide layer 124. A distance D2 between the hydrogen sensing interface 123 and a surface 214*a* of the aluminum oxide ($AlO_x$) layer 214 may range from about 200 Å to about 2 μm. Within this range, hydrogen could diffuse through the aluminum oxide ($AlO_x$) layer 214 to the hydrogen sensing interface 123 between the hydrogen-free oxide layer 122 and the metal oxide layer 124.

Next, as shown in FIG. 3B, a relationship between hydrogen concentration and a depth of a semiconductor structure is shown. The concentration of hydrogen in the semiconductor structure 300 may be analyzed by secondary ion mass spectrometry (SIMS) technology. It could be seen from FIG. 3B, hydrogen could diffuse through the aluminum oxide ($AlO_x$) layer 214, and accumulate at the hydrogen sensing interface 123 between the hydrogen-free oxide layer 122 and the metal oxide layer 124.

Figure 4:
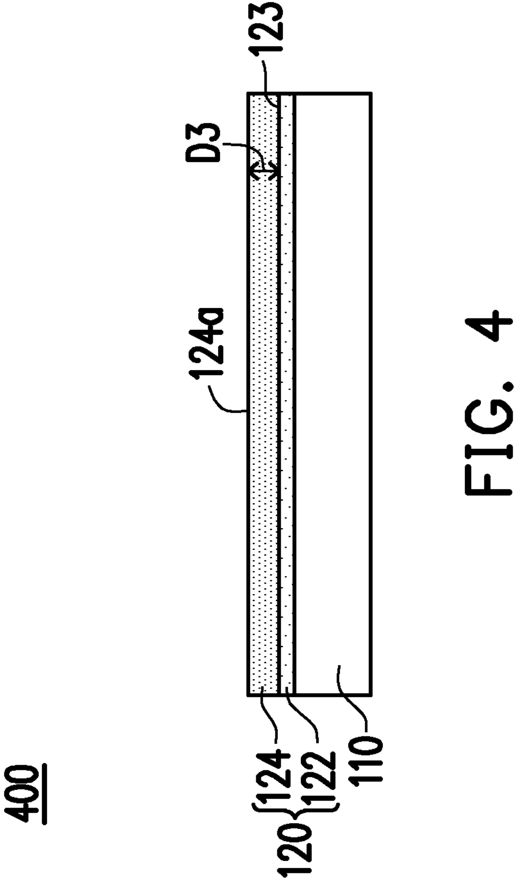
FIG. 4 illustrate schematic cross-sectional views of a semiconductor structure according to some embodiments of the present disclosure.

FIG. 4 illustrate schematic cross-sectional views of a semiconductor structure according to some embodiments of the present disclosure.

Referring to FIG. 4, the protection layer 210 may be omitted, and thus the hydrogen sensing stacked layer 120 is exposed in the atmosphere. There is a hydrogen sensing interface 123 located between the hydrogen-free oxide layer 122 and the metal oxide layer 124. In some embodiment, a distance D3 between the hydrogen sensing interface 123 and the surface 124*a* of the metal oxide layer 124 may range from about 200 Å to about 2 μm. Within this range, hydrogen could diffuse to accumulate at the hydrogen sensing interface 123 between the hydrogen-free oxide layer 122 and the metal oxide layer 124.

Figure 5:
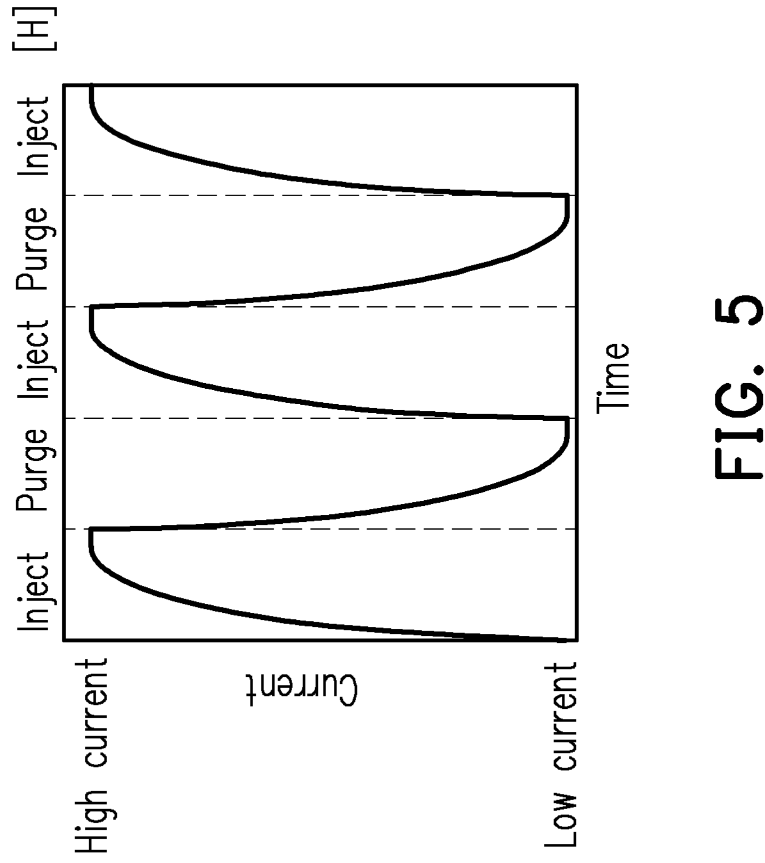
FIG. 5 illustrate a view showing a relationship between current and time of circle of hydrogen inject/purge according to some embodiments of the present disclosure.

FIG. 5 illustrate a view showing a relationship between current and time of circle of hydrogen inject/purge according to some embodiments of the present disclosure.

The hydrogen sensor has been tested several times for sensing the hydrogen gas and the corresponding analysis has been shown in FIG. 5. The relationship between current and the presence of hydrogen of the hydrogen sensor has been tested inside the closed chamber equipped with hydrogen gas injector. Within every cycle, hydrogen is injected into the chamber and then be purged. As shown in FIG. 5, the current increases when hydrogen injected in the chamber and decays when hydrogen is at the purge stage, since the resistance of the hydrogen sensing stacked layer is inversely proportional to the concentration of hydrogen gas. That is, when the hydrogen accumulates at the hydrogen sensing interface between the hydrogen-free oxide layer and the metal oxide layer, the resistance of the hydrogen sensing stacked layer decreases. Therefore, the current passing through the hydrogen-free oxide layer increases. In other words, the higher the concentration of hydrogen gas, the lower the resistance of the hydrogen sensing stacked layer, and thus the higher the conductivity of the hydrogen sensing stacked layer.

Figure 6:
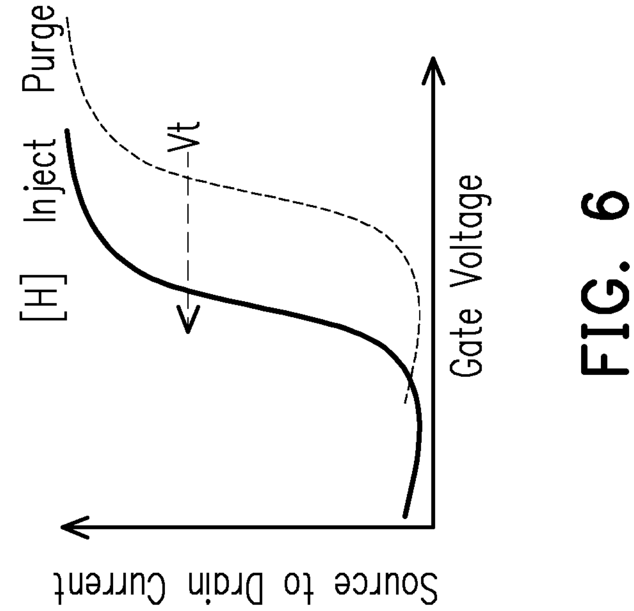
FIG. 6 illustrate a view showing a relationship between current and a threshold voltage of a hydrogen sensor according to some embodiments of the present disclosure.

FIG. 6 illustrate a view showing a relationship between current and a threshold voltage of a hydrogen sensor according to some embodiments of the present disclosure.

A hydrogen sensor having a hydrogen sensing stacked layer as shown in FIGS. 2A, 3A, and 4 is provided. The hydrogen sensor further comprises a transistor having a gate electrode, a source electrode, and a drain electrode. The hydrogen sensing stacked layer may serve as a channel layer of the transistor, and the gate electrode is in contact with the hydrogen-free oxide layer. The hydrogen sensor has been tested inside the closed chamber equipped with hydrogen gas injector, and the current from the source electrode to the drain electrode is measured. When hydrogen is injected into the chamber, the threshold voltage of the gate electrode decreases correspondingly as shown in FIG. 6. That is due to the increasing of the conductivity of the hydrogen sensing stacked layer when hydrogen accumulated at the hydrogen sensing interface.

FIGS. 7-15 illustrate schematic cross-sectional views at various stages of formation of an integrated circuit having a hydrogen sensor according to some embodiments of the present disclosure. It is understood that additional steps can be provided before, during, and after the method disclosed, and some of the steps described can be moved, replaced, or eliminated for additional embodiments of the method disclosed. In addition, additional features can be added in the integrated circuit depicted in FIGS. 7-15, and some of the features described below can be replaced, modified, or eliminated in other embodiments of the integrated circuit.

Figure 7:
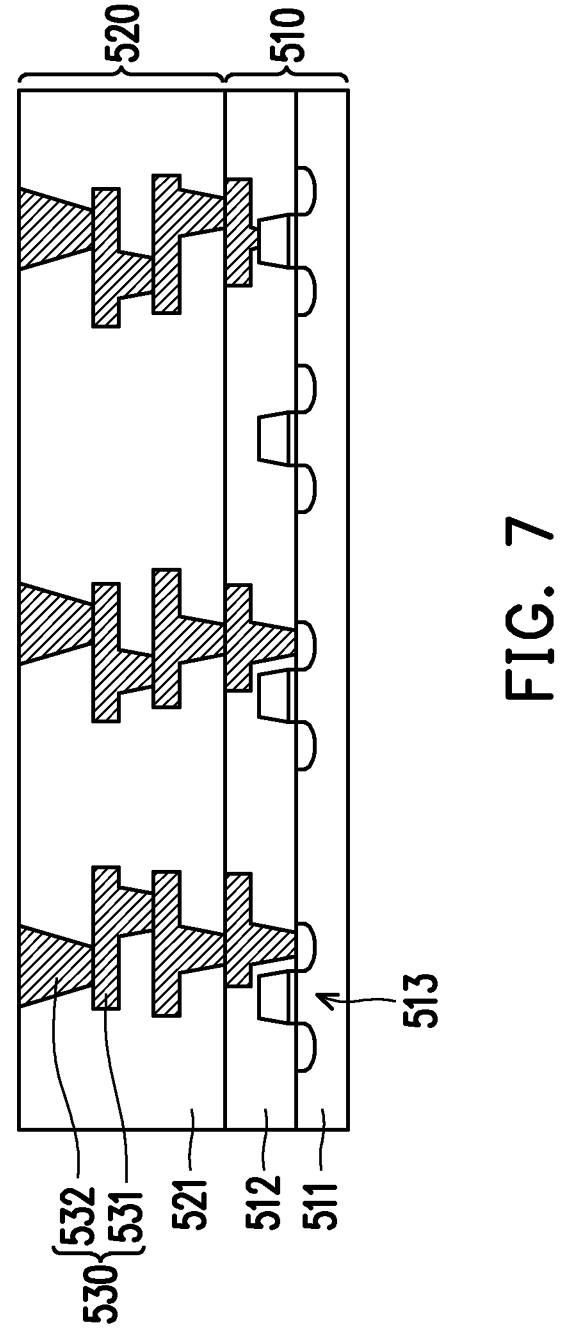
FIGS. 7-15 illustrate schematic cross-sectional views at various stages of formation of an integrated circuit having a hydrogen sensor according to some embodiments of the present disclosure.

Referring to FIG. 7, forming first stacked dielectric layers 520 on a semiconductor substrate 510. The semiconductor substrate 510 includes a substrate 511 and dielectric layer 512. In some embodiments, the substrate 511 may be or comprise silicon, polysilicon, monocrystalline silicon, silicon-germanium (SiGe), or another suitable semiconductor material.

The dielectric layer 512 may be or comprise low-k dielectric materials, silicon dioxide, other suitable dielectric material(s). In some embodiment, the dielectric layer 512 may be deposited by CVD, PVD, ALD, or another suitable growth or deposition process.

As illustrated in FIG. 7, the semiconductor substrate 510 includes various semiconductor devices 513 such as Fin-type field effect transistors (FinFETs) and/or MOSFETs may be formed on, and/or in, the substrate 511 during front-end-of-line (FEOL) processing. Various doped wells (not shown) may be formed in various regions of the upper portion of the substrate 511 by performing masked ion implantation processes. In some embodiments, the semiconductor substrate 510 includes one semiconductor device or multiple semiconductor devices. For illustrative purposes, the semiconductor substrate 510 comprises four semiconductor devices 513, as shown in FIG. 7. However, the number of the semiconductor devices 513 is not limited in the present invention.

In some embodiments, gate structures are formed over the substrate 511. In some embodiments, ion implantation processes are performed to form implant regions, which may include source regions and drain regions. In some embodiments, a semiconductor channel is formed underneath each gate structures between a neighboring pair of implant regions. Each field effect transistor 513 includes a gate structure, a semiconductor channel, and a pair of implant regions (one of which functions as a source region and another of which functions as a drain region).

The first stacked dielectric layers 520 include a dielectric layer 521 and interconnect wirings 530 embedded in the dielectric layer 521. The interconnect wirings 530 includes interconnect metal lines 531 and contact vias 532. The bottom contact vias 532 electrically connect to one of the source/drain regions or the gate electrodes of the semiconductor devices 513. The interconnect metal lines 531 and the contact vias 532 may be or comprise tungsten, ruthenium, titanium, titanium nitride, tantalum nitride, copper, aluminum, or other suitable conductive material(s).

Figure 8:
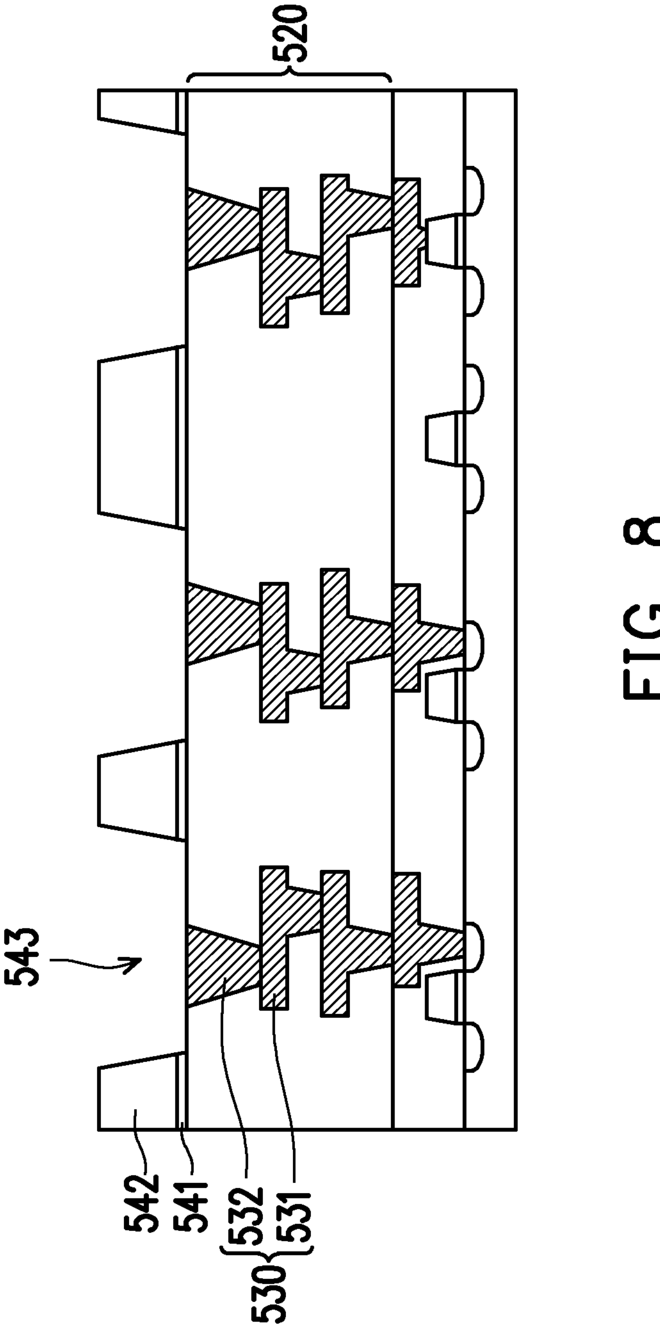

Next, as shown in FIG. 8, an etching stop layer 541 and an interlayer dielectric (ILD) layer 542 are sequentially deposited on the first stacked dielectric layers 520.

In some embodiments, the material of the etching stop layer 541 includes silicon nitride (SiN), silicon carbide (SiC), silicon oxycarbide (SiOC), silicon oxynitride (SiON), silicon carbonitride (SiCN), silicon oxycarbonitride (SiOCN), combinations thereof and/or other suitable materials. In some embodiments, the etch stop layer 541 may be formed by chemical vapor deposition (CVD), plasma-enhanced CVD (PECVD), physical vapor deposition (PVD), atomic layer deposition (ALD), or the like. In some embodiments, the ILD layer 542 includes silicon oxide, carbon-containing oxide such as SiOC, silicate glass, tetraethylorthosilicate (TEOS) oxide, un-doped silicate glass, or doped silicon oxide such as borophosphosilicate glass (BPSG), fluorine-doped silica glass (FSG), phosphosilicate glass (PSG), boron doped silicon glass (BSG), combinations thereof and/or other suitable dielectric materials. In some other embodiments, the ILD layer 542 may include low-k dielectric material with a dielectric constant lower than 4, extreme low-k (ELK) dielectric material with a dielectric constant lower than 2.5. For example, the low-k material includes a polymer-based material, such as benzocyclobutene (BCB), FLARE®, or SILK®; or a silicon dioxide-based material, such as hydrogen silsesquioxane (HSQ) or SiOF. In some embodiments, the ILD layer 542 is formed by CVD, PECVD, flowable CVD (FCVD), PVD, spin coating, or the like.

Thereafter, a gate trench 543 is formed in the etching stop layer 541 and the ILD layer 542, in accordance with some embodiments. For example, the gate trench 543 penetrates through the ILD layer 542 and the etching stop layer 541, and exposes a top surface of the first stacked dielectric layers 520. In some embodiments, the contact vias 532 at the top is exposed by the gate trench 543 such that the contact vias 532 is in physical and electrical contact with a later-formed gate electrode. In some embodiments, the formation of the gate trench 543 includes forming a patterned mask layer (not shown) over the ILD layer 542, anisotropic etching the ILD layer 542 using the patterned mask layer as a mask to form the gate trench 543. In some embodiments, an ash process is used to remove the patterned mask layer after the gate trench 543 is formed. As illustrated in FIG. 8, the gate trench 543 is formed with slant sidewalls. Alternatively, the gate trench 543 may include substantially vertical sidewalls.

Figure 9:
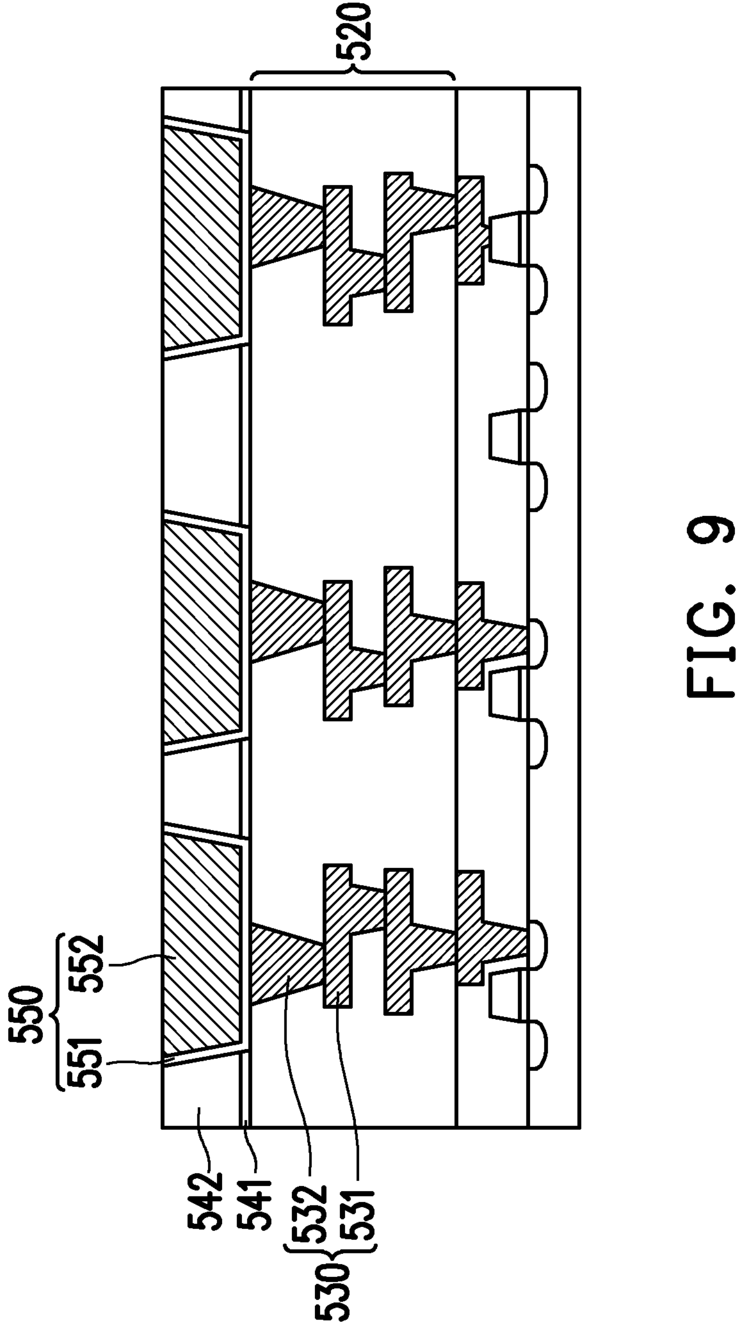

Referring to FIG. 9, a barrier material is conformally deposited over the structure shown in FIG. 8. For example, the barrier material is deposited on exposed surfaces of the contact vias 532 and the ILD layer 542 and exposed sidewalls of the gate trench 543 (see FIG. 8). In some embodiments, the barrier material includes Ta, Cu, Co, Mn, Mo, Ru, W, Au, Ag. TiN, TaN, WCN or combinations thereof, and may be formed by CVD, PECVD, ALD, or the like. Later, a gate fill material is deposited over the barrier material and fills in the gate trench 543. In some embodiments, the gate fill material includes Ta, Cu, Co, Mo, Ru, W, Au, Ag, TiN, TaN, WCN, combinations thereof, and/or other suitable metallic materials, and may be formed by CVD, PECVD, PVD, or the like. Alternatively, the formation of the gate fill material may include performing a plating process (such as electrochemical plating (ECP)).

Still referring to FIG. 9, a planarization process is then performed to remove excess barrier material and gate fill material, exposing a top surface of the ILD layer 542. The planarization process includes, for example, a chemical mechanical polishing (CMP) process or an etch back process. The remaining barrier material forms a barrier layer 551 and the remaining gate fill material forms a gate layer 552. The combination of the barrier layer 551 and the gate layer 552 that fills the gate trench constitutes a gate electrode 550. The gate electrode 550 extends through the ILD layer 542 and the etching stop layer 541 and is in direct contact with the first stacked dielectric layers 520 (e.g., in direct contact with the contact vias therein). As shown in FIG. 9, after the planarization process, a top surface of the gate electrode 550 is substantially coplanar with the top surface of the ILD layer 542.

Figure 10:
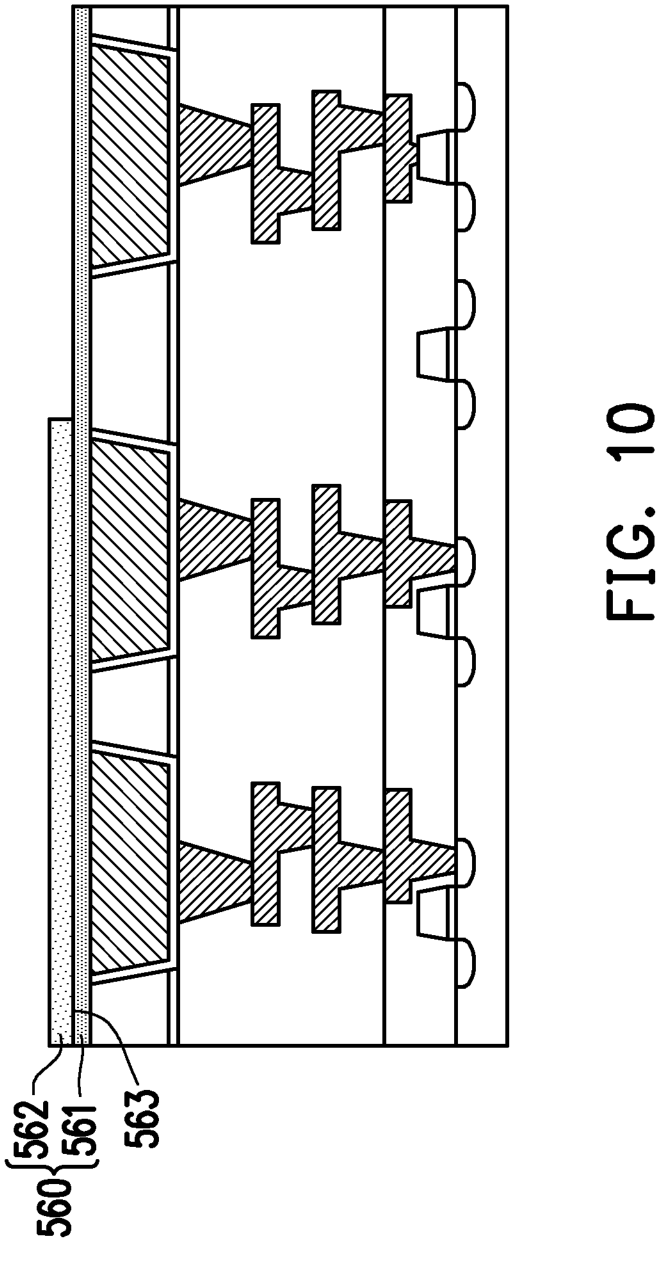

Referring to FIG. 10, a hydrogen-free oxide layer 561 and a metal oxide layer 562 are sequentially deposited over the ILD layer 542 and the gate electrode 550. For example, the hydrogen-free oxide layer 561 is formed covering top surfaces of the ILD layer 542 and the gate electrode 550, and the metal oxide layer 562 is formed covering a top surface of the hydrogen-free oxide layer 561. The hydrogen-free oxide layer 561 and the metal oxide layer 562 constitutes a hydrogen sensing stacked layer 560. The hydrogen-free oxide layer 561 is in contact with the gate electrode 550.

In some embodiment, the hydrogen-free oxide layer 561 may include silicon nitride, $Al_2O_3$, HfO, ZrO, or TiO, and may be formed by in-situ steam generation (ISSG) process. In some embodiment, the metal oxide layer 562 may include InGaZnO, InO, GaO, ZnO, AlO, SnO, or CuO, and may be formed by any suitable deposition process, such as, atomic layer deposition (ALD), chemical vapor deposition (CVD), high density plasma CVD (HDP-CVD), physical vapor deposition (PVD), and/or the like.

Thereafter, forming a patterned mask layer (not shown) over the metal oxide layer 562, anisotropic etching the metal oxide layer 562 using the patterned mask layer as a mask to exposed portion of the hydrogen-free oxide layer 561.

A hydrogen sensing interface 563 is located between the hydrogen-free oxide layer 561 and the metal oxide layer 562. Due to lack of hydrogen in the hydrogen-free oxide layer 561, weak bonding is formed at the hydrogen sensing interface 563 between the hydrogen-free oxide layer 561 and the metal oxide layer 562, and vacancies are generated at the hydrogen sensing interface 123 accordingly.

Figure 11:
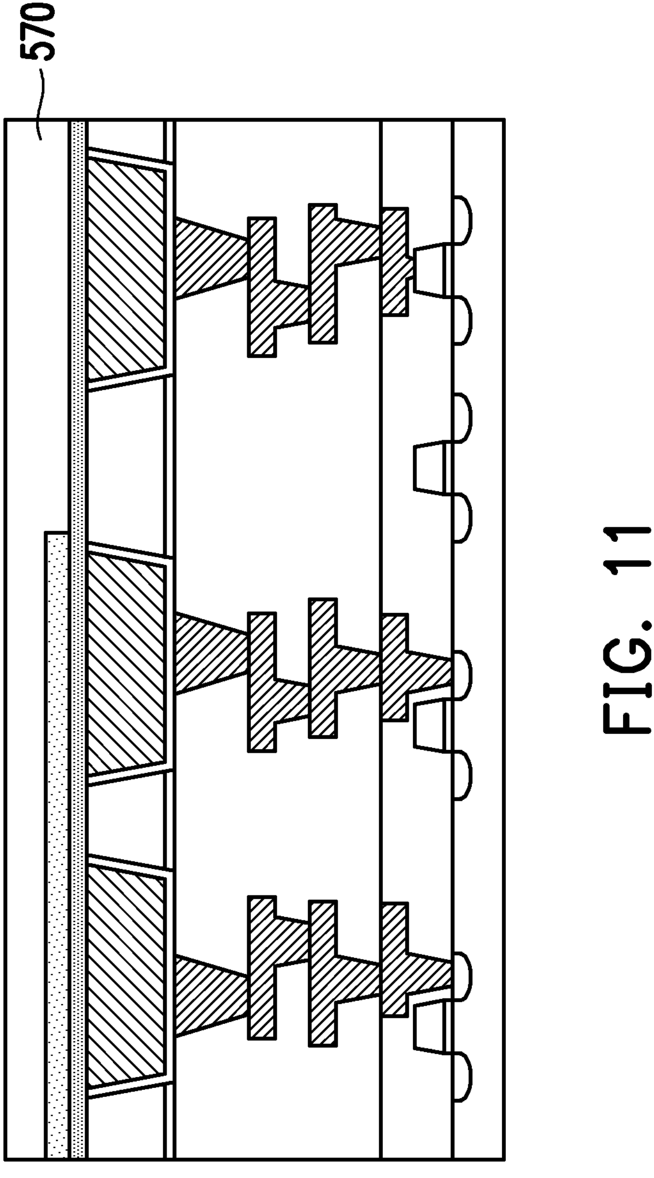

Referring to FIG. 11, a protection layer 570 formed on the hydrogen sensing stacked layer 560. For example, the protection layer 570 is deposited over the hydrogen-free oxide layer 561 and the metal oxide layer 562. Specifically, the protection layer 570 is formed covering top surfaces of the metal oxide layer 562 and the exposed portion of the hydrogen-free oxide layer 561.

In some embodiment, the protection layer 570 comprises a single layer, and the single layer comprises an aluminum oxide ($AlO_x$) layer. In some embodiment, the protection layer 570 comprises a stacked layer, and the stacked layer comprises a silicon oxide layer and an aluminum oxide ($AlO_x$) layer disposed on the silicon oxide layer. In an alternative embodiment, the protection layer 570 may be optionally omitted.

Figure 12:
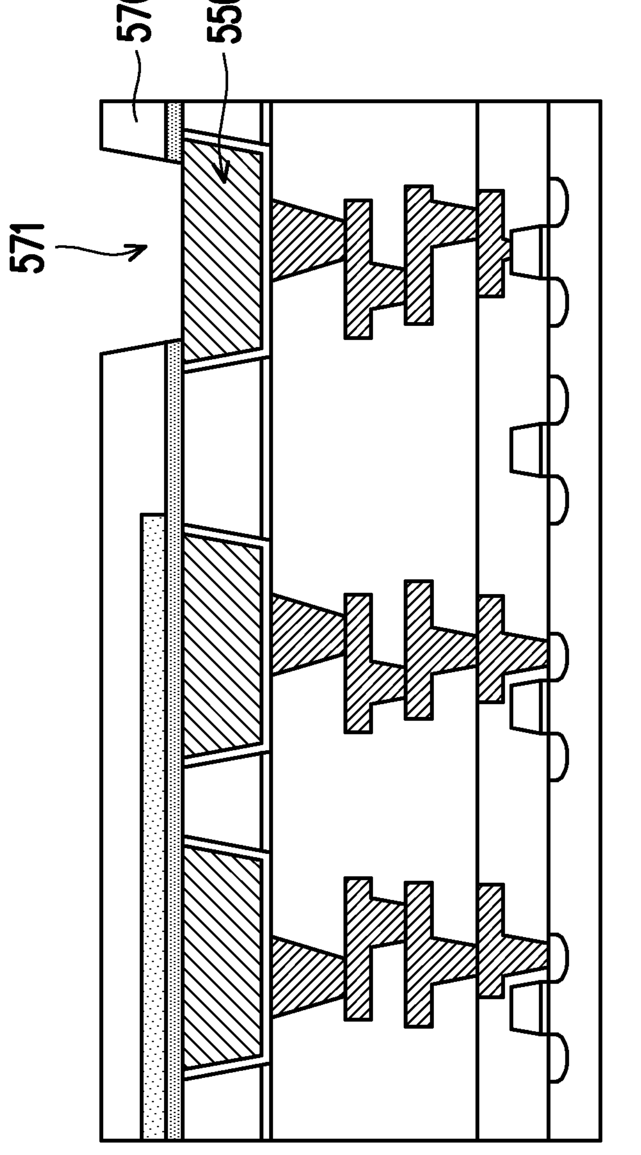

Referring to FIG. 12, an opening 571 is formed in the protection layer 570 and the hydrogen-free oxide layer 561, in accordance with some embodiments. For example, the opening 571 penetrates through the protection layer 570 and the hydrogen-free oxide layer 561 and exposes a top surface of the gate electrode 550. In some embodiments, the formation of the opening 571 includes forming a patterned mask layer (not shown) over the protection layer 570, anisotropic etching the protection layer 570 using the patterned mask layer as a mask to form the opening 571. In some embodiments, an ash process is used to remove the patterned mask layer after the opening 571 is formed. As illustrated in FIG. 12, the opening 571 is formed with slant sidewalls. Alternatively, the opening 571 may include substantially vertical sidewalls.

Figure 13:
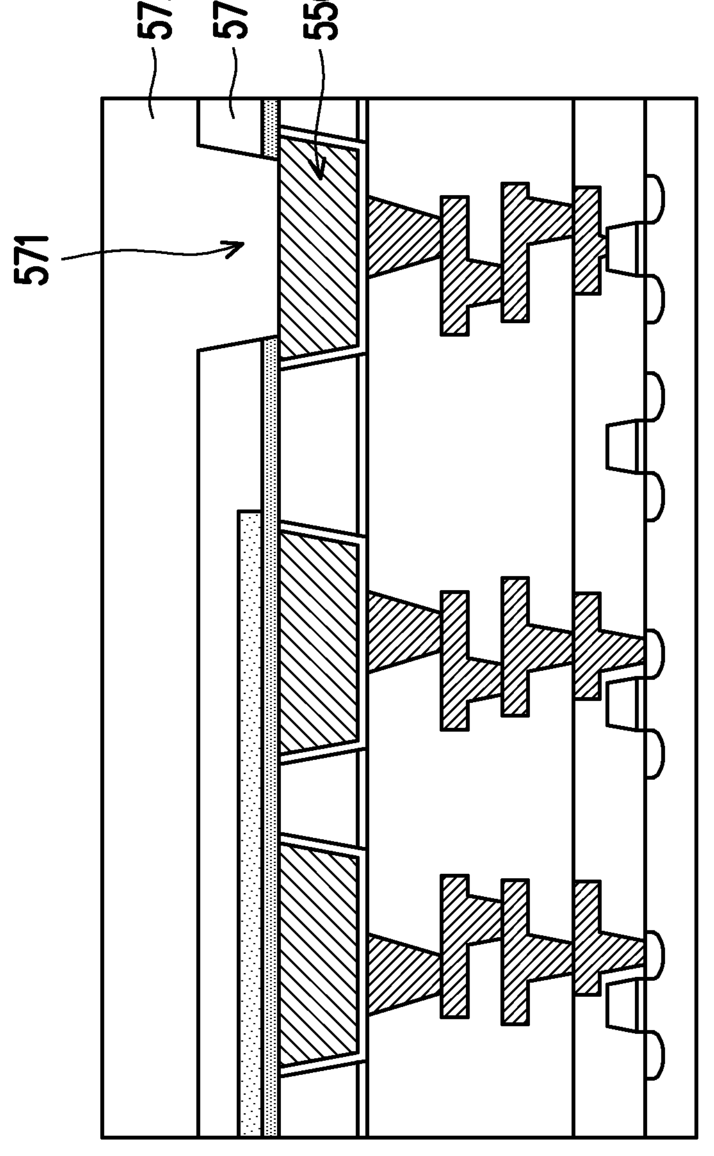

Referring to FIG. 13, an ILD layer 572 formed on the protection layer 570. For example, the ILD layer 572 is deposited over the protection layer 570 and filled in the opening 571. Specifically, the ILD layer 572 is formed covering top surfaces of the protection layer 570 and covering top surfaces of the exposed gate electrode 550. In some embodiments, the purpose of the opening 571 is to connect upper structures, which is formed at subsequent process, to the exposed gate electrode 550. For example, a via (not shown) could be formed in the ILD layer 572 and over the exposed gate electrode 550 to connect the exposed gate electrode 550 with the upper structures (not shown).

Figure 14:
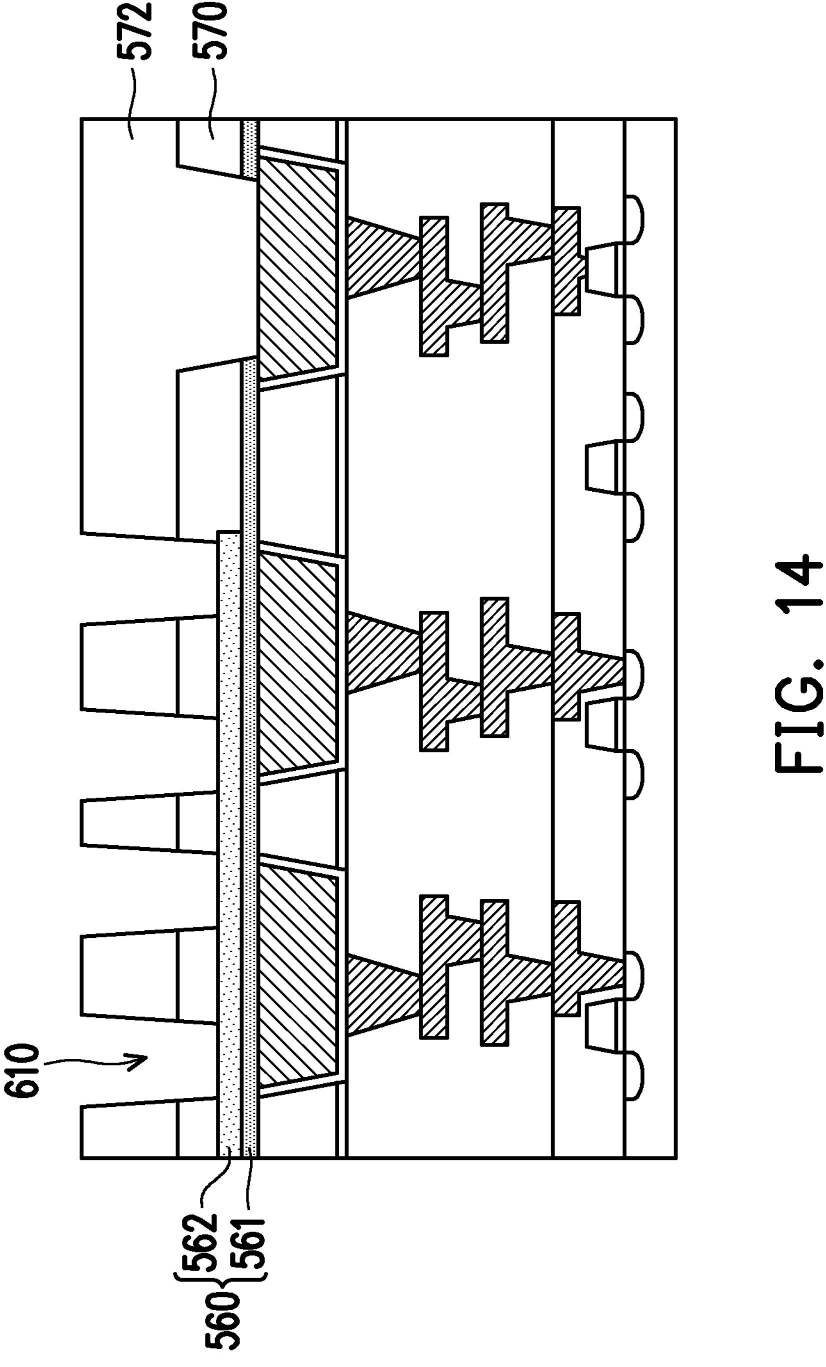

Referring to FIG. 14, an etching process is performed to expose portions of the hydrogen sensing stacked layer 560. In some embodiments, an etching process, such as a wet etching or a dry etching, or a combination thereof, is performed to form openings 610. For example, the dry etching process etches through the ILD layer 572 and protection layer 570 such that the openings 610 penetrate through the ILD layer 572 and protection layer 570.

Figure 15:
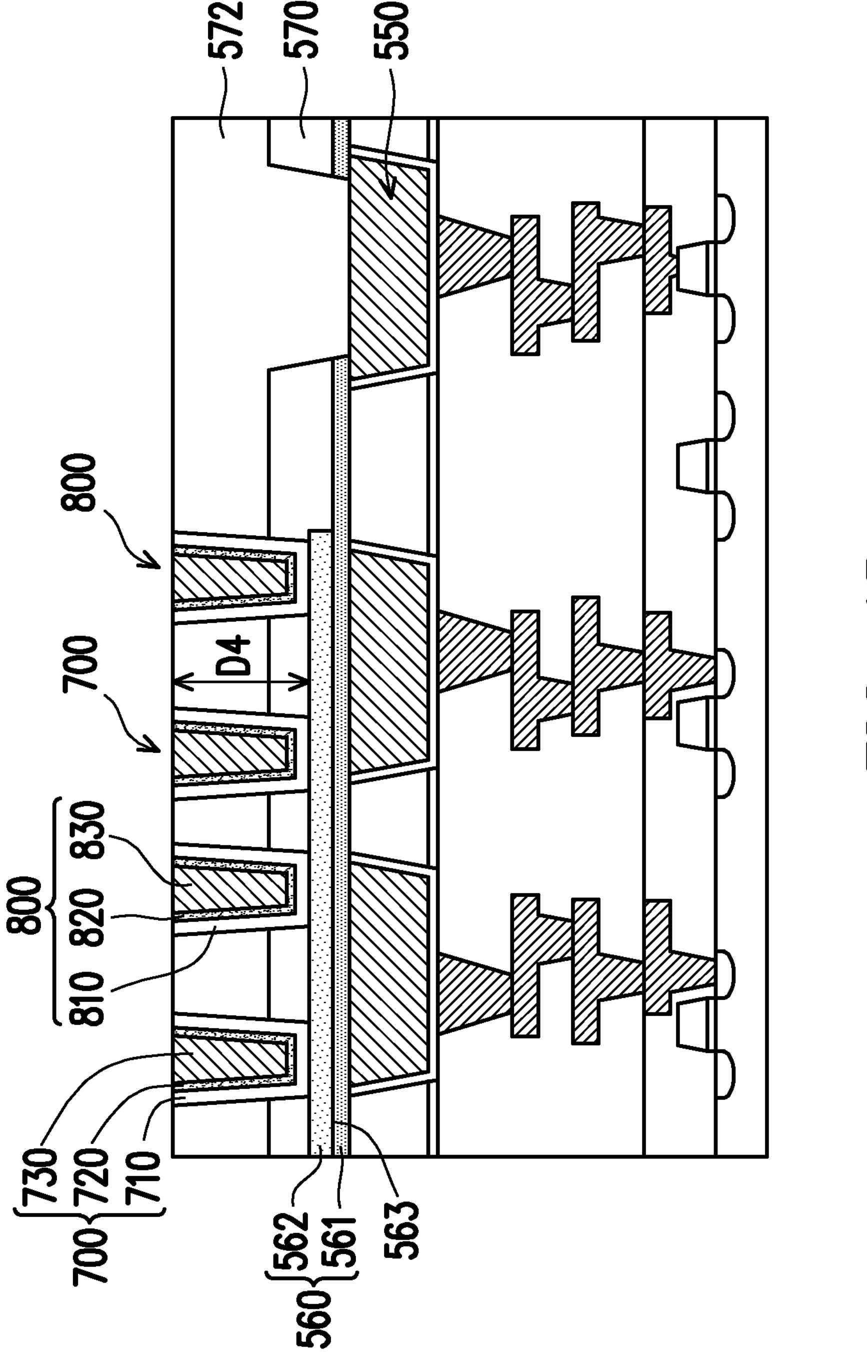

Referring to FIG. 15, source electrode 700 and drain electrode 800 are formed in the openings 610 and are in direct contact with the hydrogen sensing stacked layer 560. Each source electrode 700 and drain electrode 800 includes a barrier layer 710, 810 over the openings 610 and conformally covering the sidewalls of the openings 610 and covering the exposed surface of the hydrogen sensing stacked layer 560. Each source electrode 700 and drain electrode 800 further includes a seed layer 720, 820 formed over the openings 610 and on the barrier layer 710, 810 and metallic contact 730, 830 formed on the seed layer 720, 820 within the openings 610 and filling the openings 610. In some embodiments, the barrier layer 710, 810 is formed before forming the seed layer 720, 820 to prevent out-diffusion of the material of the seed layer 720, 820.

In some embodiments, a barrier material (not shown) and a seed material (not shown) are sequentially formed over the openings 610 and conformally covering the exposed surface of the hydrogen sensing stacked layer 560 and the sidewalls of the openings 610, and a metallic material (not shown) is then filled into the openings 610 and on the seed material. The barrier material and the seed material may individually include one or more materials selected from tungsten (W), ruthenium (Ru), molybdenum (Mo), tantalum (Ta), titanium (Ti), alloys thereof, and nitrides thereof, for example. In addition, the metallic material may include TiN, TaN, Ta, Cu, Co, Mo, Ru, W, Au, Ag, WCN, combinations thereof, and/or other suitable metallic materials. In some embodiments, the barrier material is formed by CVD, PVD or ALD. In some embodiments, the seed material is formed by CVD PVD or ALD. In some embodiments, the metallic material is formed by CVD or PVD. In alternative embodiments, the formation of the metallic material includes performing a plating process (such as ECP).

In some embodiments, a planarization process is then performed to remove excess barrier material, excess seed material, and excess metallic material. The planarization process includes, for example, a CMP process or an etch back process. The remaining barrier material forms the barrier layer 710, 810, the remaining seed material forms the seed layer 720, 820, and the remaining metallic material forms the metallic contact 730, 830. The combination of the barrier layer 710, 810, the seed layer 720, 820, and the metallic contact 730, 830 that fills the openings 610 constitutes the source electrode 700 and the drain electrode 800. As seen in FIG. 15, a top surface of the ILD layer 572 is substantially coplanar with top surfaces of the source electrode 700 and drain electrode 800.

Still referring to FIG. 15, in some embodiments, the source electrode 700 and drain electrode 800 as source and drain terminals of an obtained transistor. The hydrogen sensing stacked layer 560 functions as a channel layer of the transistor, in accordance with some embodiments. The transistor includes the gate electrode 550, the hydrogen sensing stacked layer 560 having the hydrogen-free oxide layer 561 and the metal oxide layer 562, the protection layer 570, and ILD layer 572 that are sequentially stacked from the bottom to the top. The transistor further includes source electrode 700 and drain electrode 800 which extend through the ILD layer 572 and the protection layer 570, such that bottom surfaces (contact surfaces) of the source electrode 700 and drain electrode 800 are in direct contact with the hydrogen sensing stacked layer 560, without the residue of the protection layer 570. Further, as shown in FIG. 15, a bottommost portion of each source electrode 700 and drain electrode 800 is surrounded by the protection layer 570 and the ILD layer 572. In some embodiments, a distance D4 between the hydrogen sensing interface 563 and a surface of the ILD layer 572 may range from about 200 Å to about 2 μm. Within this range, hydrogen could diffuse through the ILD layer 572 and the protection layer 570 to accumulate at the hydrogen sensing interface 563 between the hydrogen-free oxide layer 561 and the metal oxide layer 562 through dangling bond.

In various embodiment, a second stacked dielectric layers (not shown) are formed on the transistor and thus covering the ILD layer 572, the source electrode 700, the drain electrode 800, and the embedded hydrogen sensing stacked layer 560.

In accordance with an embodiment of the disclosure, a semiconductor structure is described. The semiconductor structure includes a semiconductor substrate, a hydrogen sensing stacked layer disposed over the semiconductor substrate, and a protection layer disposed on the hydrogen sensing stacked layer. The hydrogen sensing stacked layer comprises a hydrogen-free oxide layer and a metal oxide layer disposed on the hydrogen-free oxide layer.

In accordance with an embodiment of the disclosure, an integrated circuit (IC) is described. The integrated circuit includes a semiconductor substrate comprising semiconductor devices, an interconnect structure disposed on the semiconductor substrate, and a hydrogen sensor embedded in the interconnect structure. The hydrogen sensor comprises a hydrogen sensing stacked layer disposed over the semiconductor substrate, and the hydrogen sensing stacked layer comprises a hydrogen-free oxide layer and a metal oxide layer disposed on the hydrogen-free oxide layer.

In accordance with yet another embodiment of the disclosure, a method for manufacturing an integrated circuit (IC) device is described. The method includes at least the following steps. A semiconductor substrate comprising semiconductor devices is provided. An interconnect structure comprising an embedded hydrogen sensor is formed. The interconnect structure is disposed on the semiconductor substrate, the interconnect structure is electrically connected to the semiconductor devices, and a method for forming the interconnect structure is described. The method includes at least the following steps. First stacked dielectric layers are formed and interconnect wirings are formed embedded in the first stacked dielectric layer. The embedded hydrogen sensor is formed on the first stacked dielectric layers.

Also, although the disclosure has been shown and described with respect to one or more implementations, equivalent alterations and modifications will occur to others of ordinary skill in the art based upon a reading and understanding of this specification and the annexed drawings. The disclosure comprises all such modifications and alterations and is not limited thereto. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one or more of several implementations, such feature may be combined with one or more other features of the other implementations as may be desired and advantageous for any given or particular application.

What is claimed is:

1. A semiconductor structure, comprising:

a semiconductor substrate;

a hydrogen sensing stacked layer disposed over the semiconductor substrate, the hydrogen sensing stacked layer comprising a hydrogen-free oxide layer and a metal oxide layer disposed on the hydrogen-free oxide layer; and a dielectric protection layer disposed on the hydrogen sensing stacked layer.

2. The semiconductor structure of claim 1, wherein the metal oxide layer is between the dielectric protection layer and the hydrogen-free oxide layer, and the hydrogen-free oxide layer is between the semiconductor substrate and the metal oxide layer.

3. The semiconductor structure of claim 1, wherein the dielectric protection layer comprises a single layer, and the single layer comprises an aluminum oxide ($AlO_x$) layer.

4. The semiconductor structure of claim 1, wherein the dielectric protection layer comprises a stacked layer, and the stacked layer comprises a silicon oxide layer and an aluminum oxide ($AlO_x$) layer disposed on the silicon oxide layer.

5. The semiconductor structure of claim 1, wherein a hydrogen sensing interface is located between the hydrogen-free oxide layer and the metal oxide layer, and a distance between the hydrogen sensing interface and a surface of the dielectric protection layer ranges from −200 Å to −2 μm.

6. The semiconductor structure of claim 1, wherein the hydrogen-free oxide layer comprises silicon nitride, $Al_2O_3$, HfO, ZrO, or TiO.

7. The semiconductor structure of claim 1, wherein the metal oxide layer comprises InGaZnO, InO, GaO, ZnO, AlO, SnO, or CuO.

8. The semiconductor structure of claim 1, wherein the hydrogen sensing stacked layer serves as a channel layer of a transistor, the transistor further comprises a gate electrode, a source electrode, and a drain electrode, and the gate electrode is in contact with the hydrogen-free oxide layer.

9. An integrated circuit (IC), comprising:

a semiconductor substrate comprising semiconductor devices;

an interconnect structure disposed on the semiconductor substrate; and a hydrogen sensor embedded in the interconnect structure, wherein the hydrogen sensor comprises a transistor having a gate electrode, a source electrode, and a drain electrode and a hydrogen sensing stacked layer, the hydrogen sensing stacked layer serves as a channel layer of the transistor, the hydrogen sensing stacked layer comprises a hydrogen-free oxide layer and a metal oxide layer disposed on the hydrogen-free oxide layer, and the gate electrode is in contact with the hydrogen-free oxide layer.

10. The semiconductor structure of claim 9, wherein a hydrogen sensing interface is located between the hydrogen-free oxide layer and the metal oxide layer, and a distance between the hydrogen sensing interface and a surface of the metal oxide layer ranges from 200 Å to 2 μm.

11. The semiconductor structure of claim 9, wherein the gate electrode is between the hydrogen sensing stacked layer and the interconnect structure.

12. The semiconductor structure of claim 9, wherein the source electrode and the drain electrode are disposed on and electrically connected to the metal oxide layer.

13. The semiconductor structure of claim 9, further comprising:

a protection layer disposed on the hydrogen sensing stacked layer.

14. The semiconductor structure of claim 13, wherein the protection layer comprises a single layer, and the single layer comprises an aluminum oxide ($AlO_x$) layer.

15. The semiconductor structure of claim 13, wherein the protection layer comprises a stacked layer, and the stacked layer comprises a silicon oxide layer and an aluminum oxide ($AlO_x$) layer disposed on the silicon oxide layer.

16. The semiconductor structure of claim 13, wherein a hydrogen sensing interface is located between the hydrogen-free oxide layer and the metal oxide layer, and a distance between the hydrogen sensing interface and a surface of the protection layer ranges from 200 Å to 2 μm.

17. A method of manufacturing an integrated circuit (IC) device, comprising:

providing a semiconductor substrate comprising semiconductor devices; and forming an interconnect structure comprising an embedded hydrogen sensor, wherein the interconnect structure is disposed on the semiconductor substrate, the interconnect structure is electrically connected to the semiconductor devices, and a method for forming the interconnect structure comprises:

forming first stacked dielectric layers and interconnect wirings embedded in the first stacked dielectric layer;

forming the embedded hydrogen sensor on the first stacked dielectric layers; and forming second stacked dielectric layers covering the first stacked dielectric layers and the embedded hydrogen sensor.

18. The method of claim 17, wherein the method for forming the interconnect structure further comprises:

forming a protection layer on the hydrogen sensing stacked layer.

19. The method of claim 18, wherein the protection layer comprises an aluminum oxide ($AlO_x$) layer.

20. The method of claim 17, wherein the method for forming the interconnect structure further comprises:

forming a gate electrode in contact with the hydrogen-free oxide layer; and forming a source electrode and a drain electrode, wherein the source electrode and the drain electrode are disposed on and electrically connected to the metal oxide layer.

* * * * *